(12) United States Patent
Curtis (10) Patent No.: US 7,267,695 B2
(45) Date of Patent: Sep. 11, 2007

(54) FOUR HOLE OFFSET ALIGNMENT DEVICE

(75) Inventor: Michael J. Curtis, Green Bay, WI (US)

(73) Assignee: American Prosthetic Components, Inc., Green Bay, WI (US)

( * ) Notice: Subject to any disclaimer, the term of this patent is extended or adjusted under 35 U.S.C. 154(b) by 294 days.

(21) Appl. No.: 10/876,349

(22) Filed: Jun. 25, 2004

(65) Prior Publication Data

US 2005/0288798 A1  Dec. 29, 2005

(51) Int. Cl.
*A61F 2/80* (2006.01)
(52) U.S. Cl. .................................................. 623/38
(58) Field of Classification Search ............ 623/27–38
See application file for complete search history.

(56) References Cited

U.S. PATENT DOCUMENTS

| 5,047,063 A | * | 9/1991 | Chen ............................ 623/38 |
| 5,290,313 A | | 3/1994 | Heldreth |
| 5,549,710 A | * | 8/1996 | Vera et al. ..................... 623/38 |
| 5,759,206 A | * | 6/1998 | Bassett ......................... 623/27 |
| RE36,521 E | | 1/2000 | Hiemisch |
| 6,576,022 B2 | * | 6/2003 | Meyer et al. ................. 623/38 |

OTHER PUBLICATIONS

Hosmer Dorrance Corporation, product brochure, pp. H127-H132, publication date unknown.
Otto Bock, product description of lower limb prosthetics adapters, viewed at www.ottobockus.com/products/op_adapters.asp on Oct. 22, 2003. (Three pages).

* cited by examiner

*Primary Examiner*—Bruce Snow
(74) *Attorney, Agent, or Firm*—Brannen Law Office, LLC (57) ABSTRACT

The present invention relates to a four hole offset alignment device that is adjustable in the lateral or medial direction and the anterior or posterior direction at a single interface between the two pieces of the present invention. A first piece is provided having a body with a central axis. A positioner is on the first side of the body. A dome with a pyramid is on the second side of the body. A second piece is provided having a central axis and a flange. Four walls upstand from the flange to define an opening. The positioner can be selectably received within the opening while the central axis of the first piece remains parallel to the central axis of the second piece. The pieces are lockable in place with respect to each other at the selected offset alignment.

7 Claims, 8 Drawing Sheets

PRIOR ART

FOUR HOLE OFFSET ALIGNMENT DEVICE

BACKGROUND OF THE INVENTION

The present invention relates to a four hole offset alignment device, and more particularly a four hole alignment device that is adjustable in both the lateral or medial direction and the anterior or posterior direction at a single interface between the two pieces of the present invention.

DESCRIPTION OF THE RELATED ART

Sometimes, due to accidents, health problems, birth defects, etc., people 5 need to have a limb 6 amputated. The amputated limb 6 terminates in a stump 7. In general, a prosthetic component such as a socket 10 can be formed for a particular stump 7. Sockets 10 are well known in the art, and each socket 10 has an end 111 and a central axis 12.

Fortunately for people requiring a prosthetic limb, much advancement has been made in the field of prosthetic limbs. Patients now have many choices, including endoskeletal and exoskeletal prosthetic limbs. The present invention relates to endoskeletal prosthetic limbs. That is, limbs comprised of structural components and an optional aesthetic outer shell.

Figure 1:
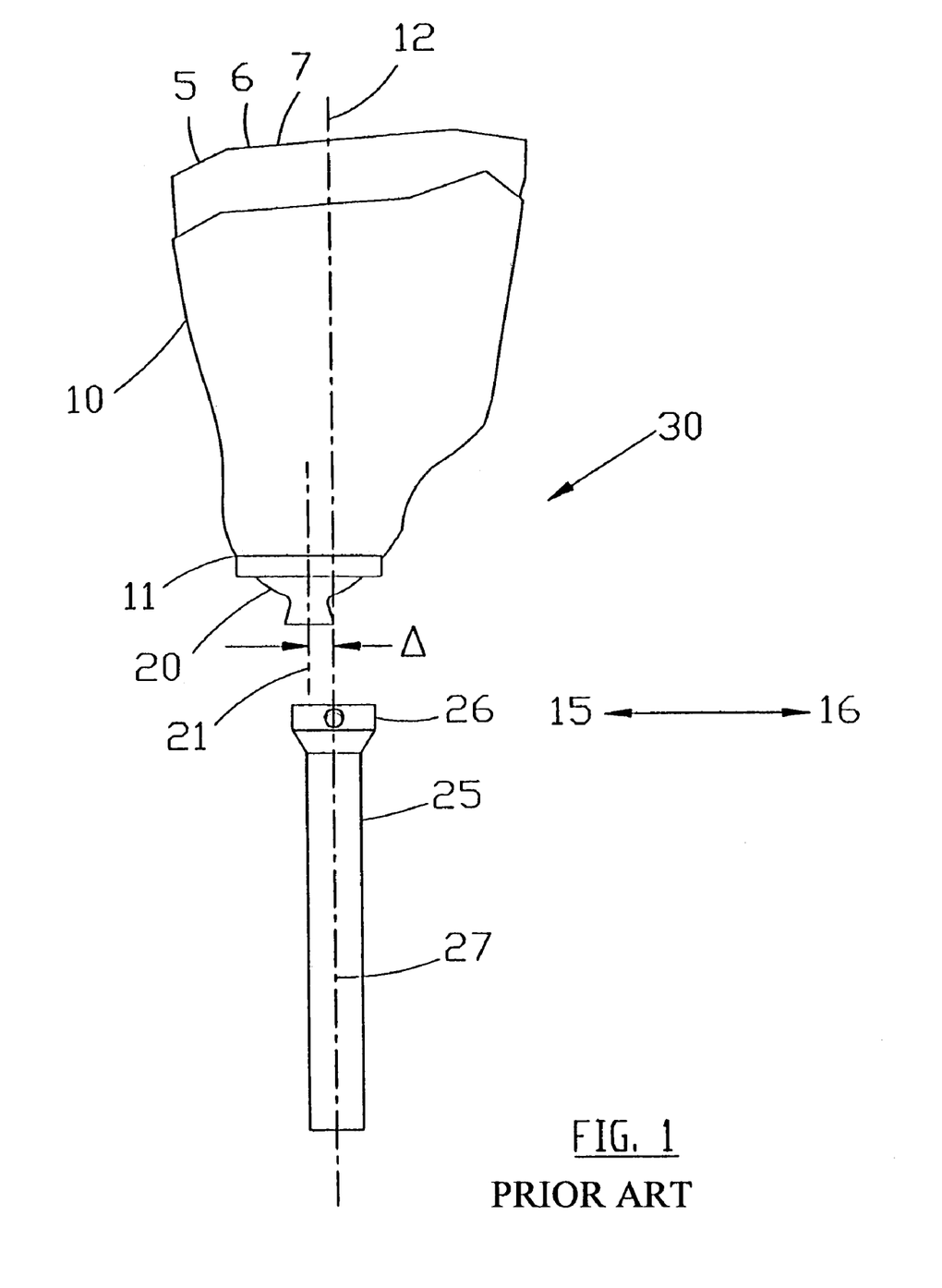
FIG. 1 is an exploded side view of existing prosthetic components.

Turning now to FIG. 1, the components of a typical prosthetic limb setup 30 are shown. A conventional four hole adapter 20 having a central axis 21 that runs centrally through the component is shown. In some situations, the four hole adapter 20 cannot be positioned centrally upon the socket 10. Even though the central axis 21 of the adapter 20 is parallel to the central axis 12 of the socket 10, it is offset there from. Specifically, the adapter central axis 21 can be offset from the socket central axis 12 in the lateral or medial direction 15 and 16 as well as in the anterior or posterior direction 18 or 19 by a total offset distance delta. A conventional pylon 25 with a fixed receiver 26 and central axis 27 is also provided. It is preferable that the pylon central axis 27 be centrally aligned with the socket central axis 12, to ensure maximum comfort and stability of the prosthetic limb. This alignment is further preferred because a person's gait may be adversely affected if the pylon central axis 27 is out of central alignment with the socket central axis 12 and the person may experience unnecessary muscle strain and fatigue. Yet, as shown, it can be impossible to achieve this preferred socket central axis 12 and pylon central axis 27 alignment when the conventional four hole adapter 20 is offset from the socket.

Similar problems also arise when the prosthetic components are attached to the lower knee joint (not shown) as opposed to a socket 10.

Figure 2:
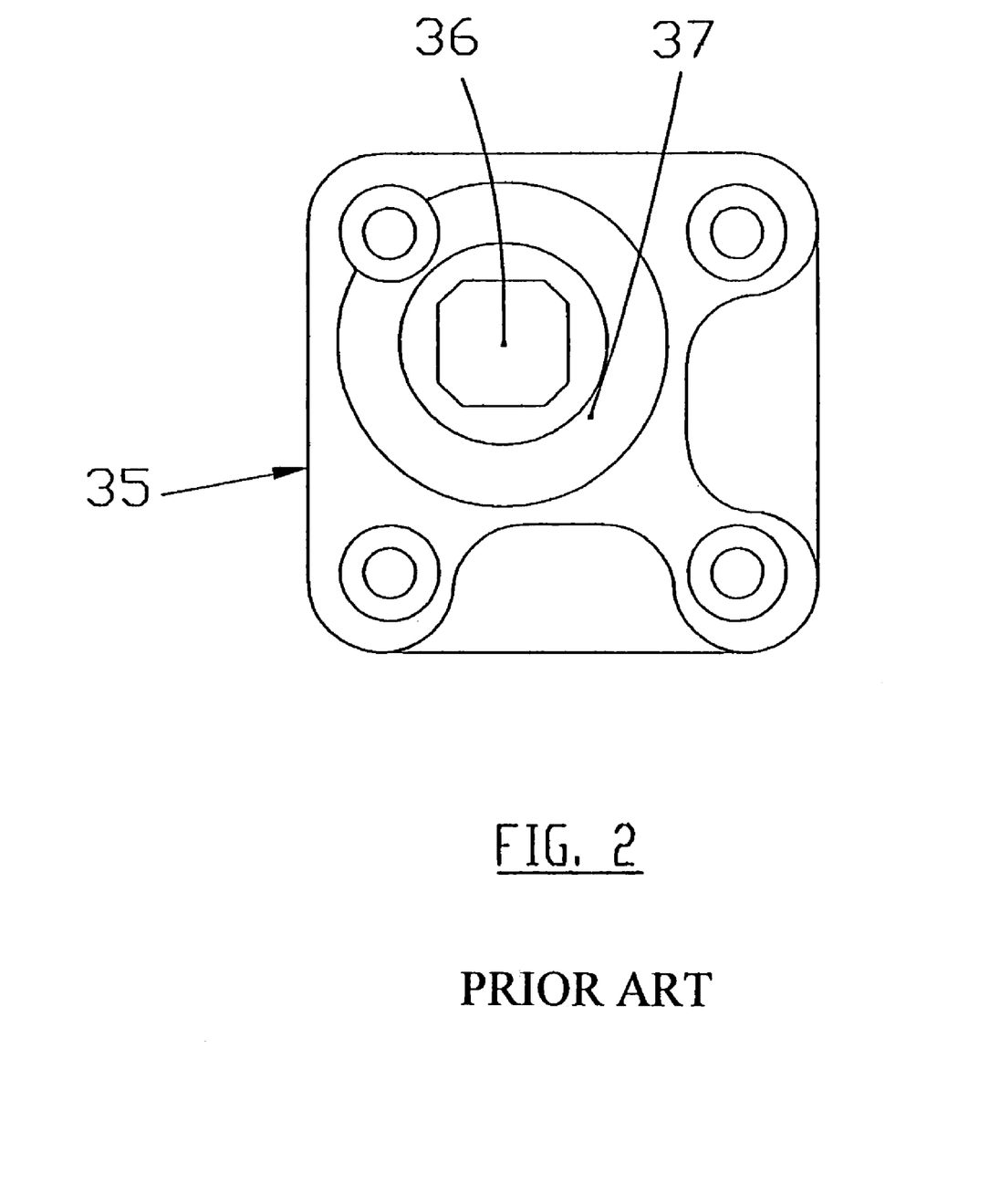
FIG. 2 is a top view of an existing rigid and offset four hole adapter.

Turning now to FIG. 2, a modified four hole adapter 35 is shown. The adapter 35 is exemplary of the adapter shown in U.S. Pat. No. RE 36,521 to Hiemisch. The modified four hole adapter 35 has a pyramid with an alignment axis 36 running there through. Adapter 35 also has a central axis 37. The alignment axis 36 and central axis 37 are parallel and offset from one another by a fixed distance and orientation. The four holes are arranged in a square pattern, such that the adapter 35 can align with its adjacent component in one of four positions by rotating the adapter 35 around its central axis 37 in relation to the adjacent component. Therefore, the alignment axis 36 can be selectively oriented to one of four distinct orientations relative to the central axis or its adjacent component.

Even though the modified adapter 35 of the Hiemisch patent may work well for its intended purposes, it is not without drawbacks. For example, while the component is capable of being reoriented with respect to an adjacent component, there are only a limited number of possible orientations. Specifically, only four orientations are possible. Further, the adapter 35 is only useful when the offset amount delta is at an appropriate distance and angle from the socket central axis 12 in a plane defined by the lateral or medial direction 15 and 16 and the anterior or posterior direction 17 and 18. In many prosthetic limbs, the end of the socket 11 is not offset by an amount that can be overcome with adapter 35. Therefore, incorporation of the adapter 35 into the prosthetic limb may not work to fully realize its intended results.

A further existing product is made by Hosmer Dorrance Corporation under the name Spectrum Alignment System. To make adjustments in both the lateral or medial direction and also the anterior or posterior direction, a minimum of three major components is required. The first component is a four hole plate with a male dovetail protruding there from along a first axis. The second component is an adapter with a female dovetail receiver for mating with the male dovetail of the first component, and with a male dovetail that is on the opposed side of the adapter and that is aligned generally perpendicular to the female dovetail receiver. The third component has a female dovetail receiver on its first side for mating with the male dovetail of the second component and a standard pyramid on the opposed side.

To make adjustments with the Spectrum Alignment System, side shift screws are provided. Each side shift screw has a head with a rib that rests in a groove in the female dovetail section. The threaded end of the screw is received within a hole in the male dovetail section. The screw head remains laterally stationary relative to the female dovetail section as the screw is twisted. However, the male dovetail section translates towards or away from the screw head as the screw is twisted, depending on which way the screw is twisted. Three screws and ball bearings are shown to guide the male end within the female end. The ball bearings are anti-friction devices that reduce friction between the female and male dovetail sections, which encourage movement of the male end within the female end when the side shift screw is twisted.

The structural integrity of the dovetail connection is determined solely by the strength of the ribs on the screw head. If the screw head fails, the entire component could fail. These components may therefore be less than optimally strong. Also, given that three components are necessary to effectuate the intended adjustment, this system is undesirably overly complicated.

Thus there exists a need for a four hole offset alignment device that solves these and other problems.

SUMMARY OF THE INVENTION

The present invention relates to a four hole offset alignment device that is adjustable in the lateral or medial direction and the anterior or posterior direction at a single interface between the two pieces of the present invention.

This is accomplished by providing a first piece having a body with a central axis through the body. The body has two sides. A positioner is on the first side of the body. A dome with a pyramid is on the second side of the body. A second piece, having a central axis and a flange is also provided. Four walls upstand from the flange to define an opening.

The first and second pieces of the present invention are selectably offsetable at a single interface in both the lateral or medial direction and in the anterior or posterior direction. The first piece and second piece co-act so that the positioner can be selectably received and positioned within the opening. The body of the first piece rests on the top of the walls of the second piece to provide stability and ensure that the central axis of the first piece remains parallel to the central axis of the second piece.

It is a goal of the present invention to have only limited complexity. This is accomplished by having only two major pieces that are adjustable in both the lateral or medial direction and the anterior or posterior direction at a single interface.

It is a further goal of the present invention to have a prosthetic component that is precisely adjustable. This is accomplished by incorporating screws in the preferred embodiment that can precisely adjust alignment of the pieces in both the lateral or medial direction and in the anterior or posterior direction.

A further goal of the present invention is to provide maximum comfort and stability to a person with a prosthetic limb. This is accomplished by allowing the prosthetic limb to be properly aligned to enable the person to have a correct gait.

A still further goal of the present invention is to provide a prosthetic component that is strong enough to withstand daily stresses that it is subject to. This is accomplished in the preferred embodiment by having the body of the first piece rest on the walls of the second piece to ensure proper alignment of the first piece central axis and the second piece central axis, and by having multiple screws to forceably keep the positioner within the opening.

Other advantages, benefits, and features of the present invention will become apparent to those skilled in the art upon reading the detailed description of the invention and studying the drawings.

DETAILED DESCRIPTION OF THE PREFERRED EMBODIMENTS

While the invention will be described in connection with a preferred embodiment, it will be understood that it is not intended to limit the invention to that embodiment. On the contrary, it is intended to cover all alternatives, modifications and equivalents as may be included within the spirit and scope of the invention as defined by the appended claims.

The present invention is a four hole alignable device 50. The device, or prosthetic component, is connectable to an adjacent prosthetic component, such as a socket 10 or a lower knee joint. The device 50 is also connectable to a prosthetic component, such as a conventional pylon 25 or other type of component having a pyramidal receiver. However, it will be understood that these adjacent prosthetic components are exemplary in nature, and that the present invention is not limited for use therewith. The four hole alignable device 50 of the present invention is preferably made of Titanium allow. However, other materials may be used without departing from the broad aspects of the present invention. The present invention is preferably made in a Computer Numerical Controlled machining process.

Figure 3:
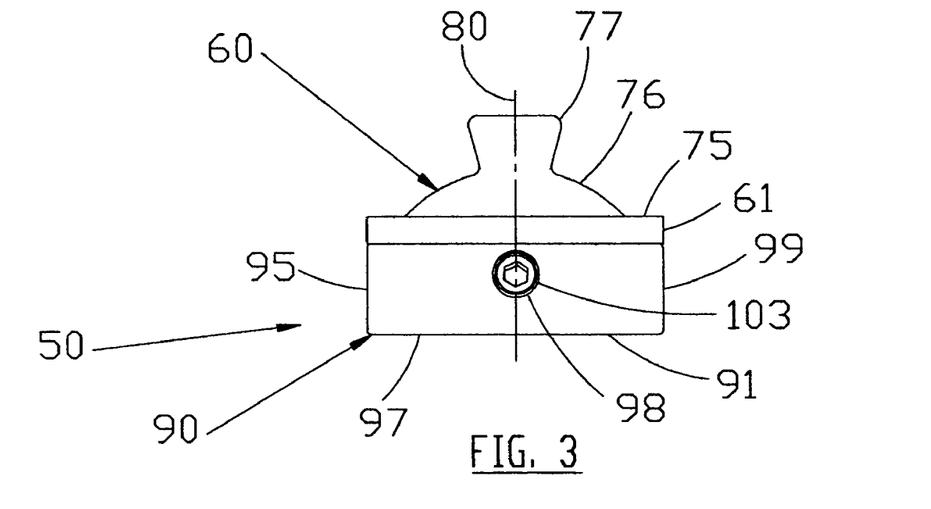
FIG. 3 is a side view of an embodiment of the present invention.
Figure 4:
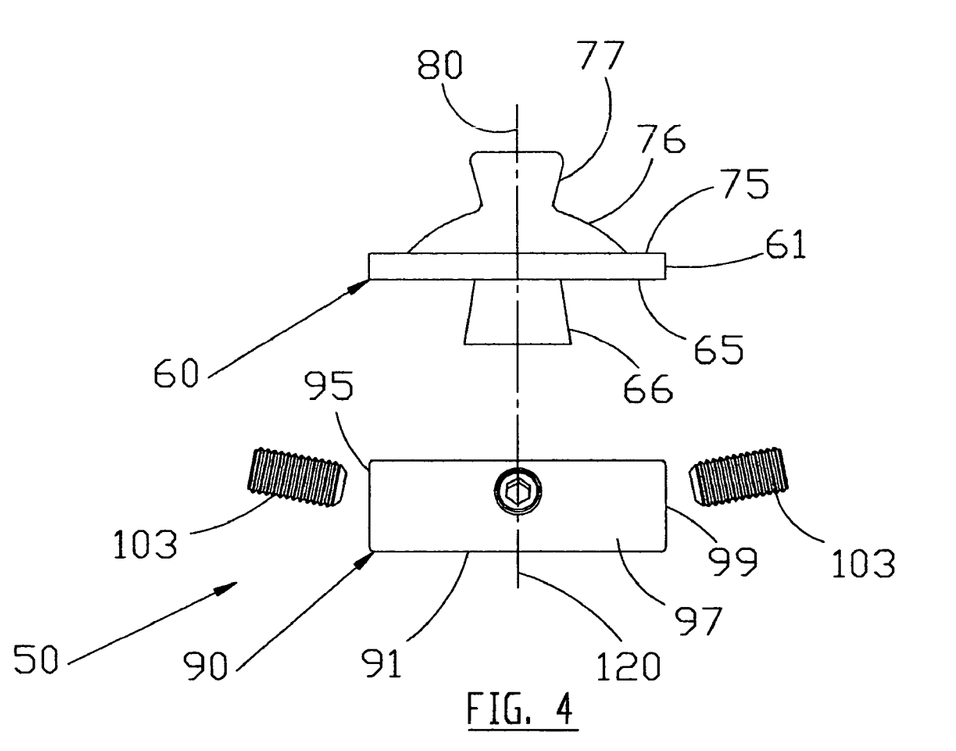
FIG. 4 is an exploded side view of the embodiment shown in FIG. 3.
Figure 5:
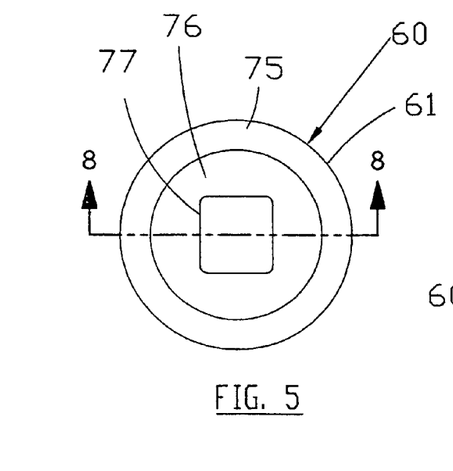
FIG. 5 is a top view of an embodiment of a piece of the present invention.
Figure 6:
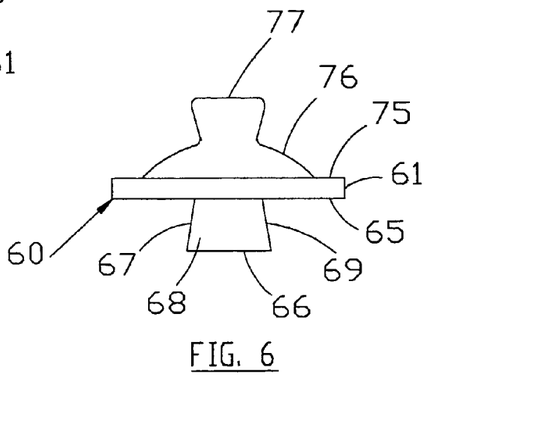
FIG. 6 is a side view of the piece shown in FIG. 5.
Figure 7:
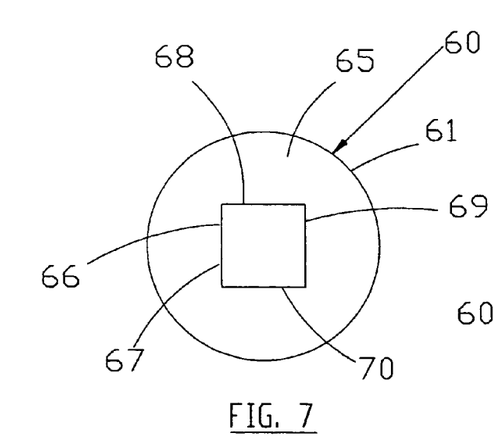
FIG. 7 is a bottom view of the piece shown in FIG. 5.
Figure 8:
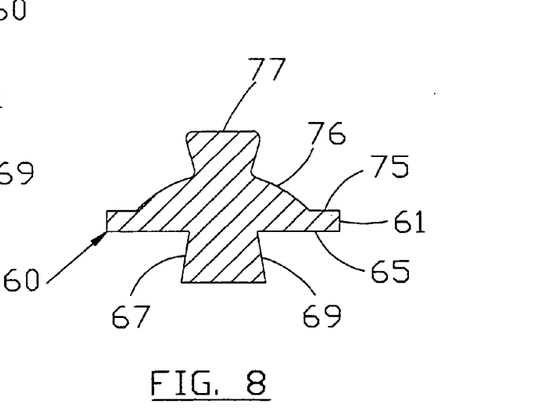
FIG. 8 is a cross-sectional view of the piece shown in FIG. 5 taken along line 8-8 in FIG. 5.

Turning now to FIGS. 3 and 4, it is shown that the four hole alignable device 50 is comprised of two major pieces 60 and 90, respectively.

The first piece 60, or component, is shown in further detail in FIGS. 5-8. The first piece 60 has a body 61. Body 61 is preferably a flat flange that lies in a plane and that is disk shaped. Body 61 has a first side 65 and an opposed second side 75. A central axis 80 runs through the first piece in a direction generally perpendicular to the body 61.

A positioner 66 is on the first side 65 of the body 61. The positioner 66 is preferably a protrusion that is formed integral with the first side. Further, the positioner 66 preferably has the shape of a four sided pyramid with faces 67, 68, 69 and 70. Face 67 opposes face 69, and face 68 opposed face 70. The pyramid has an outer surface that lies in a plane that is generally parallel to the plane of the body.

A dome 76 with a pyramid 77 is preferably on the second side 75 of the body 61 of the first piece 60. The dome 76 and pyramid 77 are preferably conventional in nature, and are adapted to be connected to an adjacent prosthetic component. In the preferred embodiment, the dome 76 and pyramid 77 are formed integral with the body 61. It is understood that an alternative connector can be used without departing from the broad aspects of the present invention.

Figure 9:
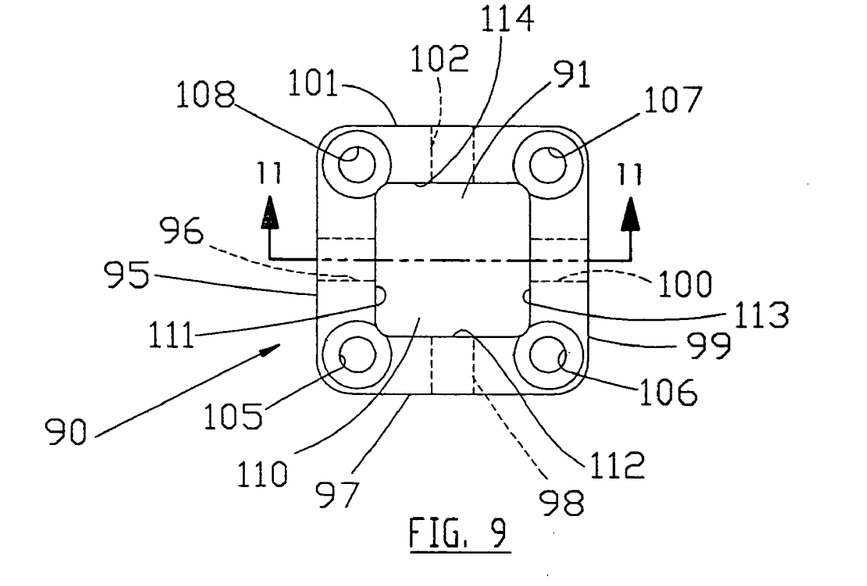
FIG. 9 is a top view of an embodiment of a second piece of the present invention.
Figure 10:
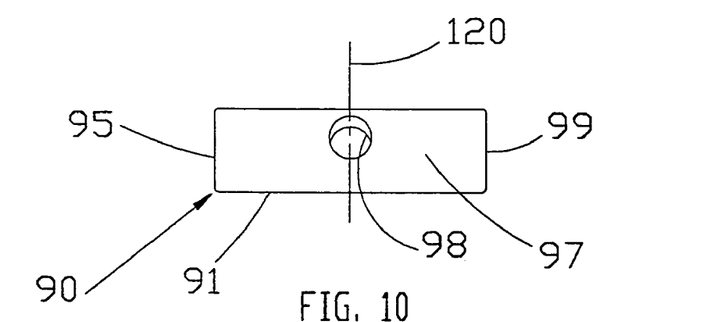
FIG. 10 is a side view of the piece shown in FIG. 9.
Figure 11:
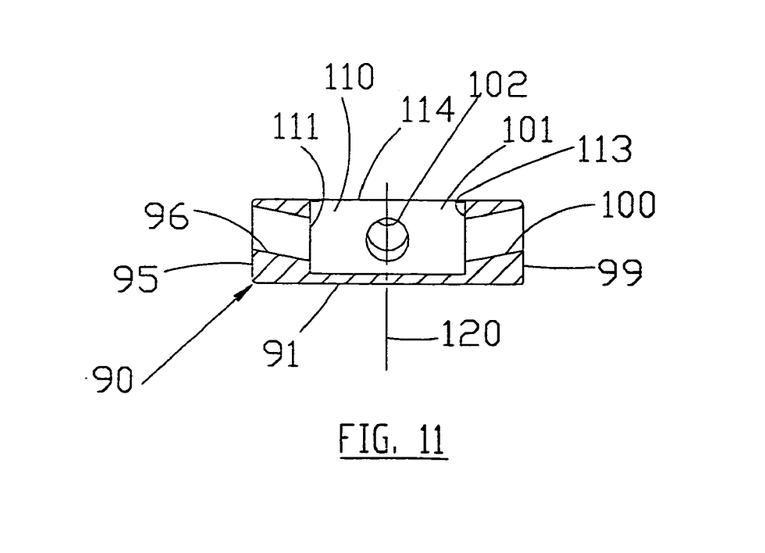
FIG. 11 is a cross-sectional view of the piece shown in FIG. 9 taken along line 11-11 in FIG. 9.

Turning now to FIGS. 9-11, a second piece 90 is shown in further detail. The second piece 90, or component, has a flange 91. The flange 91 is preferably flat, and lies in a plane. The perimeter of the flange 91 is preferably square shaped. Four walls 95, 97, 99 and 101 upstand from the flange 91, preferably at the perimeter of the flange. Wall 95 is opposed to wall 99, and wall 97 is opposed to wall 101. The four walls 95, 97, 99 and 101 are preferably integral with the flange 91 and preferably each lie in a plane generally perpendicularly to the flange plane. The walls 95, 97, 99 and 101 define an opening 110, discussed in further detail below. A central axis 120 extends through the second piece 90. The central axis 120 is generally perpendicular to the flange plane and generally parallel to plane of each wall 95, 97, 99 and 101, respectively.

A hole 96 extends through wall 95. A second hole 98 extends through wall 97. A third hole 100 extends through wall 99. A fourth hole 102 extends through wall 101. Each hole 96, 98, 100 and 102 preferably has a respective hole axis that intersects the flange plane at a location inward of the respective wall, as best shown in FIG. 11. Holes 96, 98, 100 and 102 are adapted to receive screws 103. The screws 103 can be selectively turned into or out of the respective holes 96, 98, 100 and 102.

Holes 105, 106, 107 and 108 extend through the second piece 90 at the intersection of adjacent walls 95, 97, 99 and 101. Hole 105 is located at the intersection of walls 95 and 97. Hole 106 is located at the intersection of walls 97 and 99. Hole 107 is located at the intersection of walls 99 and 101. Hole 108 is located at the intersection of walls 101 and 95. The holes are generally perpendicular to the flange plane. The hole are preferably used to connect the second piece to an adjacent prosthetic component in the conventional manner.

The walls 95, 97, 99 and 101 define an opening 110, as best shown in FIG. 9. The opening is preferably a square shaped opening, having a depth equal to the wall height. The opening has four sides 111, 112, 113 and 114. Side 111 is comprised of the inside of wall 95. Side 112 is comprised of the inside of wall 97. Side 113 is comprised of the inside of wall 99. Side 114 is comprised of the inside of wall 101. Side 111 is opposed to side 113, and side 112 is opposed to side 114.

It is understood that there may be a different number of walls upstanding from the flange. Specifically, there may be three walls that form a triangular opening. There may also be more than four walls. Further, there may be only one circular wall. Yet, it has been found that having four walls defining a square opening allows for the preferable combination of high adjustability with minimal weight.

Figure 12:
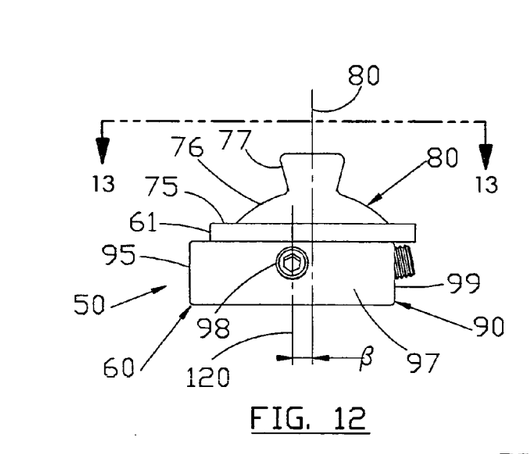
FIG. 12 is a side view of an embodiment of the present invention similar to FIG. 3, but instead showing the first piece and second piece in an offset alignment.
Figure 13:
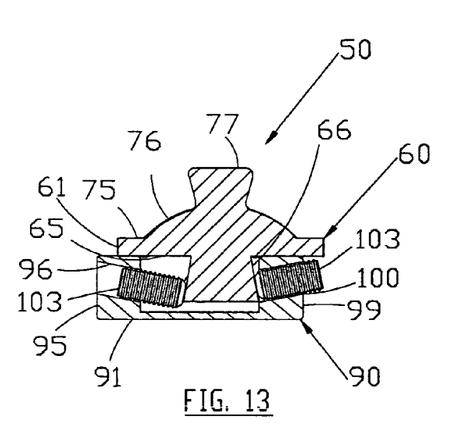
FIG. 13 is a cross-sectional view of the embodiment shown in FIG. 12 taken along line 13-13 in FIG. 12.
Figure 14:
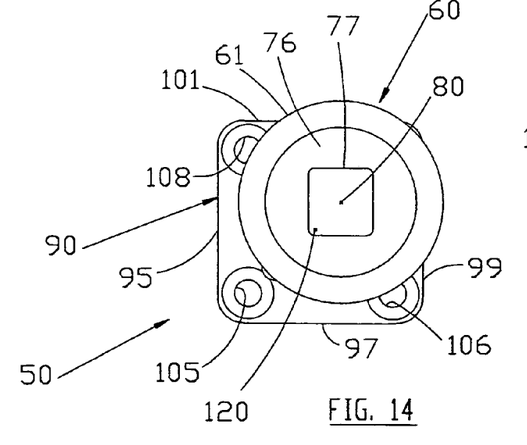
FIG. 14 is a top view of the embodiment shown in FIG. 12.

Turning now to FIGS. 12-14, an example of the co-action between the first piece 60 and second piece 90 is shown. The positioner 66 of the first piece 60 is received within the opening 110 of the second piece 90. The body 61 rests atop the top of the walls 95, 97, 99 and 101. Screws 103 received within walls 95, 97, 99 and 101 penetrate the opening 110 to engage the positioner 66. In the preferred embodiment shown, the screw 103 through hole 96 engages face 67 of the pyramidal positioner 66. Screw 103 through hole 98 engages face 68 of the pyramidal positioner 66. Screw 103 through hole 100 engages face 69 of the pyramidal positioner 66. Screw 103 through hole 102 engages face 70 of the pyramidal positioner 66. The walls 95, 97, 99 and 101 have a height that allows a screw 103 to penetrate the opening to engage the positioner to effectuate the maximum offset amount without contacting the flange 91 in this regard the protrusion can contact up to two of the walls 95, 97, 99, and 101 simultaneously.

The central axis 80 of the first piece 60 and the central axis 120 of the second piece 90 can be offset by an offset amount beta. The offset amount beta is comprised of any combination of components from the lateral or medial direction 15 or 16, respectively, and from the anterior or posterior direction 17 or 18, respectively. Described another way, the offset amount beta is comprised of a linear amount at a certain angle from the anterior direction 15 (or any other reference direction). Adjustment of the present invention to achieve a desired offset amount beta occurs at a single interface.

It is further seen that the central axis 80 of the first piece 60 and the central axis 120 of the second piece are generally parallel, even when offset by offset amount beta. In the preferred embodiment, this parallel alignment is maintained and the overall component is structurally strengthened by having the body 61 of the first piece 60 rest atop the walls 95, 97, 99 and 101 of the second piece. The body 61 is preferably a disk shaped flange to ensure that a large portion of the body 61 contacts the walls while also minimizing the overall weight of the component. The preferred disk shape, as shown in FIGS. 12 and 13, also acts to prevent any screws 103 extending out from the second piece 90 from being hit, knocked or otherwise damaged.

The preferred geometry of the positioner 66, a pyramid, is shown being engaged by screws in FIG. 13. The screws 103 force the positioner 66 to remain within the opening due to the pyramidal geometry by forcing the body 61 to be more tightly held atop the walls 95, 97, 99 and 101 of the second piece 90. The tighter the screws 103 engage the positioner 66, the stronger the component 50 is and the greater the component's ability to maintain the preferred parallel alignment between the first piece central axis 80 and the second piece central axis 120.

Figure 15:
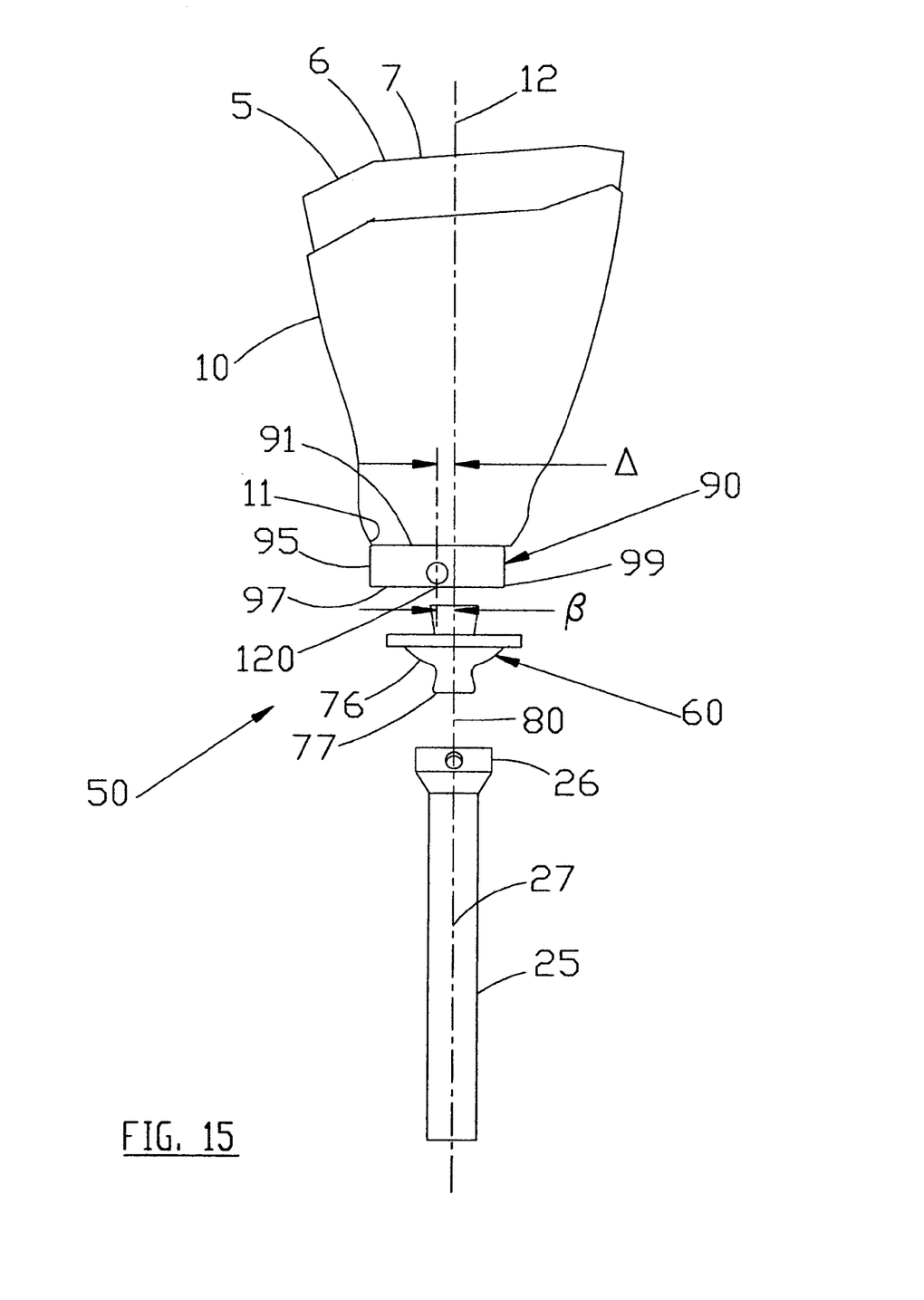
FIG. 15 is an exploded side view of an embodiment of the present invention in relation to other prosthetic components.
Figure 16:
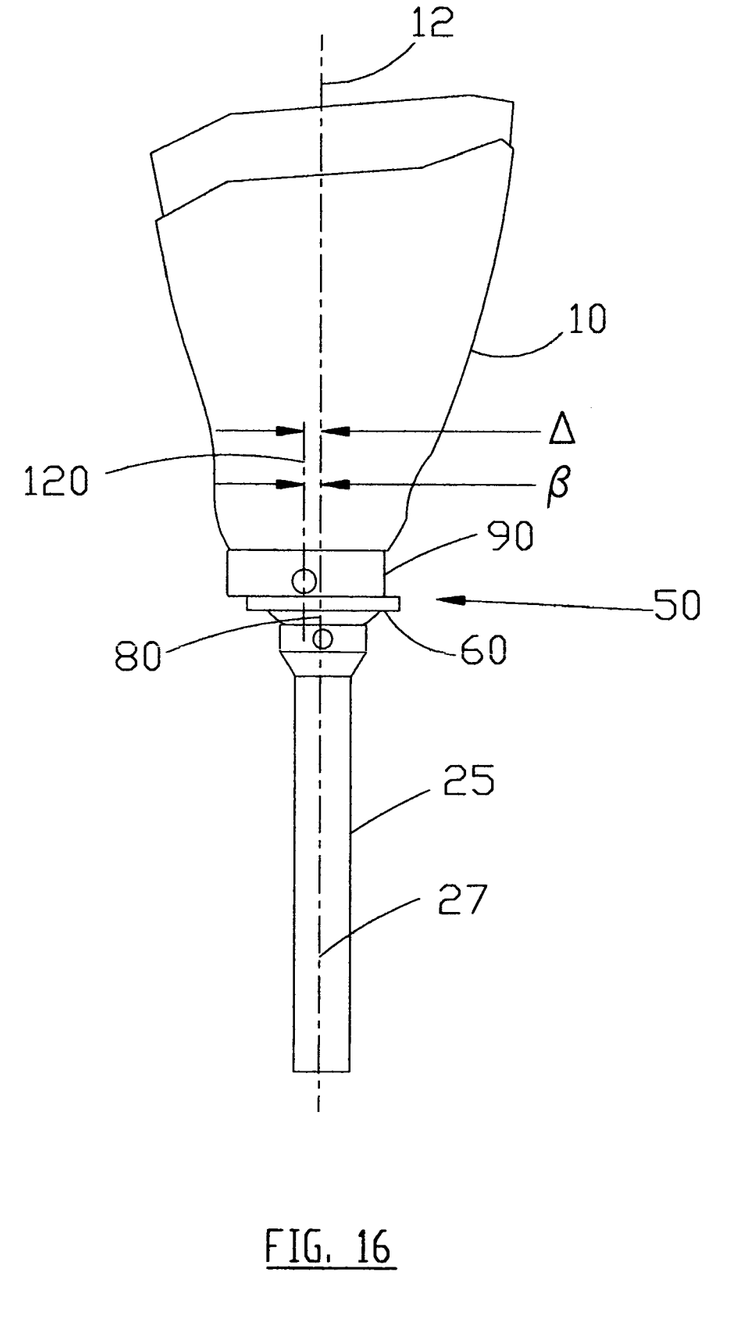
FIG. 16 is a side view of an embodiment of the present invention where the first and second pieces are offset to overcome a natural offset of the remainder of the prosthetic components.

FIGS. 15 and 16 show one application of the present invention used to overcome an offset amount between a socket central axis 12 and the central axis of a component attached thereto by an offset amount delta. Even though FIG. 15 only shows two dimensions, the offset amount delta is comprised of a distance in both the lateral or medial direction 15 or 16, respectively, and the anterior or posterior direction 17 or 18, respectively. In FIG. 15, the first piece 60 of the present invention is attached to the socket 10.

In order for the central axis 27 of the pylon 25 to be centrally aligned with the central axis 12 of the socket 10, the second piece 90 must be offset from the first piece by an offset amount beta that is equal and opposite of the offset amount delta between the socket 10 and the first piece 60.

Such adjustment is made at a single interface between the first piece 60 and the second piece 90 of the present invention. This is accomplished in the preferred embodiment by selectively positioning the positioner 66 within the opening 110 by selectively turning selected screws a selected amount into the opening 110 and turning the opposed screw a selected amount out of the wall to move or reposition the positioner to a selected orientation. This process can be enacted between both sides 111 and 113 and sides 112 and 114 to obtain the desired offset amount in both the lateral or medial direction 15 or 16 and the anterior or posterior direction 17 or 18, respectively.

Thus it is apparent that there has been provided, in accordance with the invention, a four hole offset alignment device that fully satisfies the objects, aims and advantages as set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims.

I claim:

1. A prosthetic component comprising:
A. a second piece comprising a flange lying in a plane and having four walls upstanding from said flange, wherein:
i. said second piece has four holes there through at respective intersections of said four walls and through said flange for being connectable to an adjacent prosthetic component;
  ii. said four walls define an opening; and
  iii. each of said four walls has a hole there through for receiving a screw; and
B. a first piece comprising:
  i. a body with a first side and a second side;
  ii. a positioner on said first side of said body; and
  iii. a dome with a centrally positioned pyramid on said second side of said body,
wherein said positioner is receivable within said opening and is smaller in size than said opening to enable said positioner to be selectively and adjustably placed within said opening,
wherein said positioner is fully movable within said opening to a selected location whereby the positioner can contact up to two of said four walls simultaneously, and
wherein said hole through each of said four walls is angled relative to said flange so that the screws can hold said positioner in the selected location without contacting the body of said first piece.

2. The prosthetic component of claim 1 wherein:
A. said second piece has a central axis that is generally perpendicular to said plane defined by said flange;
B. said first piece has a central axis; and
C. said central axis of said first piece and said central axis of said second piece are parallel and adjustably offset at a single interface to a selected orientation with respect to said plane defined by said flange.

3. The prosthetic component of claim 1 wherein said opening is a generally square shaped opening.

4. The prosthetic component of claim 3 wherein said positioner is a generally pyramidal shaped positioner.

5. The prosthetic component of claim 1 where engagement between said first piece and said second piece occurs between said body of said first piece and said flange of said second piece, whereby said dome of said first piece is usable free from obstructions by said second piece.

6. The prosthetic device of claim 1, wherein in an offset alignment between said first piece and said second piece, said body of said first piece is offset further relative said four walls of said second piece than the screw though said respective hole through one of said four walls.

7. A method of aligning a prosthetic limb comprising the steps of:
A. providing a first prosthetic component with a first prosthetic component central axis;
B. providing a second prosthetic component with a second prosthetic component central axis;
C. providing an alignment device with:
  i. a second piece with four holes for connecting to the first prosthetic component, and having a second piece central axis, and having four walls upstand from a flange to define an opening, each of the four walls having a hole there through; and
  ii. a first piece connectable to the second prosthetic component and having a body with a protrusion extending from the body for being received with the opening of the second piece, and having a first piece central axis;
D. positioning the protrusion of the first piece in the opening of the second piece at a single interface to centrally align the second prosthetic component central axis with the first prosthetic component central axis by compensating for misalignment between the first prosthetic component central axis and the first piece central axis in both the lateral or medial direction and the anterior or posterior direction, the range of the position being limited only by contact of the protrusion against up to two of the wall; and
E. locking the first piece in position with respect to the second piece , the locking consisting of placing screws through each of the four walls, the screws engaging the protrusion only and not the body of the first piece regardless of the location of the protrusion within the opening,
wherein:
the step of providing an alignment device with a first piece further comprises providing a dome on the body opposite the protrusion; and
the method further comprising the step of connecting the second prosthetic component to the first prosthetic component wherein movement of the second prosthetic component on the dome is uninhibited by any portion of the second piece of the alignment device.

* * * * *